(12) United States Patent
Luan et al.

(10) Patent No.: US 7,767,250 B2
(45) Date of Patent: Aug. 3, 2010

(54) BIOCERAMIC COATING OF A METAL-CONTAINING SUBSTRATE

(75) Inventors: Benli Luan, London (CA); Jianhui Xie, Windsor (CA)

(73) Assignee: National Research Council of Canada, Ottawa, Ontario (CA)

( * ) Notice: Subject to any disclaimer, the term of this patent is extended or adjusted under 35 U.S.C. 154(b) by 1084 days.

(21) Appl. No.: 11/452,962

(22) Filed: Jun. 15, 2006

(65) Prior Publication Data

US 2007/0289876 A1    Dec. 20, 2007

(51) Int. Cl.
*B05D 3/10* (2006.01)
*A61K 6/083* (2006.01)
*A61L 27/32* (2006.01)
*A61L 2/28* (2006.01)

(52) U.S. Cl. .............. 427/2.1; 427/2.26; 427/2.27; 427/532; 623/23.57; 623/23.6

(58) Field of Classification Search ........ 427/2.1–2.31, 427/532
See application file for complete search history.

(56) References Cited

U.S. PATENT DOCUMENTS

| 2,213,907 | A |  | 9/1940 | Mertes |  |
|---|---|---|---|---|---|
| 6,129,928 | A |  | 10/2000 | Sarangapani et al. |  |
| 6,541,022 | B1 | * | 4/2003 | Murphy et al. | 424/422 |
| 2002/0018798 | A1 |  | 2/2002 | Sewing et al. |  |
| 2003/0171820 | A1 | * | 9/2003 | Wilshaw et al. | 623/23.12 |
| 2004/0033249 | A1 |  | 2/2004 | Sewing et al. |  |
| 2005/0000819 | A1 | * | 1/2005 | LeGeros et al. | 205/104 |
| 2005/0170070 | A1 | * | 8/2005 | Layrolle et al. | 427/2.1 |

OTHER PUBLICATIONS

Tsuchiya et al. "Hydroxyapatite growth on anodic TiO2 nanotubes". Journal of Biomedical Materials Research. vol. 77A pp. 534-541. Feb. 16, 2006.*
Lin et al., Surface and Coatings Technology, vol. 200, Issues 12-13, pp. 3665-3669 (Mar. 31, 2006).
Bigi et al., Key Engineering Materials, vol. 284-286, pp. 223-226 (2005).
Bigi et al., Biomaterials, 26(19):4085-4089 (2005).
Lin et al., Materials Chemistry and Physics, vol. 87, No. 1, pp. 24-30 (Sep. 15, 2004).
Ma et al., Nanotechnology, vol. 14, No. 6, pp. 619-623 (Jun. 2003).

(Continued)

*Primary Examiner*—Timothy H Meeks
*Assistant Examiner*—Cachet I Sellman
(74) *Attorney, Agent, or Firm*—Hans Koenig

(57) ABSTRACT

A process for coating a surface of a metal-containing substrate with a bioceramic material includes activating the surface of the metal-containing substrate by applying a voltage to the substrate in a liquid containing an electrolyte; and, immersing the substrate in a deposition solution containing the bioceramic material or precursors for the bioceramic material. The coated substrate may be heat treated to enhance coating bond strength. The bioceramic material may be hydroxyapatite. Coated substrates are useful for the fabrication of prostheses.

22 Claims, 6 Drawing Sheets

OTHER PUBLICATIONS

Bangcheng et al., Biomaterials, 25(6):1003-1010 (Mar. 2004).
Tas et al., Journal of Materials Research, 19(9):2742-2749 (Sep. 2004).
Metodija et al., Journal of Materials Science: Materials in Medicine, 12(6):479-483 (2001).
Stigter et al., Biomaterials, 23(20):4143-4153 (2002).
Habibovic et al., Journal of the American Ceramic Society, 85(3):517-522 (2002).
Lim et al., Ceramics International, 28(1):37-41 (2002).
Liu et al., Key Engineering Materials, vol. 192-195, pp. 71-74 (2001).

* cited by examiner

BIOCERAMIC COATING OF A METAL-CONTAINING SUBSTRATE

FIELD OF THE INVENTION

The present invention is related to coating of a metal-containing substrate with a bioceramic material.

BACKGROUND OF THE INVENTION

Materials implanted in vivo essentially have direct contact with the human body through the interface between the implant surface and bones, tissues and extracellular body fluids. The surface of the implant therefore plays a very important role related to surface chemistry, topography and micro/nano structure, and tribological properties. Major issues related to surface modification processes include corrosion and wear resistance of the implant and biocompatibility and bioactivity. Chloride ion concentration in body fluid is 113 mEql$^{-1}$ and in interstitial fluid is 117 mEql$^{-1}$, which may corrode metallic materials. Body fluids contain amino acids and proteins that tend to accelerate corrosion. Toxicity and allergy occur if metallic materials are corroded by fluid, if metallic ions are released into the fluid for a long time, or if ions combine with biomolecules such as proteins and enzymes. Loosening of implant could occur due to the wear of the implant. All of these factors lead to premature implant failures, debilitating pain, and surgical revisions.

Both corrosion and wear are related to the surface of implants. Extensive studies have been reported on surface modifications to understand and enhance the performance of implants. One approach is to modify the surface topography by creating a rough or porous surface on the implant to increase the surface area available for bone/implant apposition, which improves the fixation of the implant in the bone. A natural consequence of increasing the surface area is an increase in metal ion release, due to an increased surface contact with corrosive media. A further complication is the increase in wear debris due to increased surface friction, which also results in increased ion release rates and loosening of the implants. Another approach to surface modification is to coat the implant surface with hard materials focusing on increasing the wear resistance. Titanium nitride was extensively reported for implant surface modification using chemical vapor deposition (CVD) and physical vapor deposition (PVD). Although these methods provide the implant articulating surfaces with excellent wear resistance, the deposited layers often suffer from lack of adherence and are not associated with bone/implant apposition. Low energy nitrogen ion bombardment-plasma nitriding is one of the most up-to-date methods for improving the wear and corrosion behavior of metallic alloy. In plasma nitriding, a Ti-based substrate is directly involved in the reaction of coating formation, which results in an excellent adhesion of the coating to the substrate. However, the inherent high cost of plasma nitriding equipment and its operation reduces its cost-effectiveness.

Other surface coatings have been tried to improve the bone/implant interface bonding. These include hydroxyapatite (HA) coatings produced by plasma spray or ion implantation. Hydroxyapatite, $(Ca_{10}(PO_4)_6(OH)_2)$, is characterized by a hexagonal structure (a=9.423 Å, c=6.875 Å, Space Group: P6$_3$m) with a density of 3.16 g/cm$^3$. It is one of the three main components of the human body (HA, water and collagen) and is able to integrate bone structure and support bone ingrowth. For this reason, coatings of hydroxyapatite are often applied to metallic implants to alter the surface properties. In this manner the body sees the hydroxyapatite-type material as a compatible material. Without the coating, the body would see a foreign body and either isolate it from surrounding tissues or induce a tissue reaction.

However, HA coatings formed by plasma spray, the most popular commercially available technique for HA coating on implants, generated some long term concerns. A study has revealed that even though uncemented HA-coated hip prostheses had better survivorship than cemented, the HA cups with follow-up longer than 6 years revealed an increased surgical revision rate (replacement of the primary implant). Also in a study about polyethylene wear, osteolysis and acetabular loosening with HA-coated prostheses, there were no stem revisions but 24% of the acetabular components required revision. HA debris might accelerate the wear of the high density polyethylene material (HDPE) of the acetabular component. Another study of HA coating on a G.B. acetabular cup found a high rate of debonding and failure. Yet another study reporting on the evaluation of 6 revisions of HA-coated acetabular cups showed HA granules embedded in the HDPE, which may produce severe clinical problems.

There are a variety of known techniques to produce HA coatings on substrate surfaces. Plasma spray advantageously produces high density coatings, but disadvantageously is a line-of-sight process and oxidation of powder when conducted in air leads to poor adhesion and low purity coating. High velocity oxyfuel advantageously provides good coating bond strength, but disadvantageously is a line-of-sight process and produces low purity coatings. Ion bean assisted deposition advantageously uses low deposition temperature, provides high adhesion and provides good control of stress level, microstructure and composition, but disadvantageously is a line-of-sight process and is higher in cost. Pulsed laser deposition advantageously provides high purity coatings, but disadvantageously is a line-of-sight process, requires high capital investment and maintenance costs and provides a low deposition rate. Chemical vapor deposition advantageously is not line-of-sight dependent, readily provides coatings at near theoretical density and permits control of preferred grain orientation and grain size, but disadvantageously is a high temperature process in most cases leading to low purity HA coatings. Electrodeposition is advantageously low cost and simple and provides uniform coatings of high purity and low porosity, but disadvantageously is a line-of-sight process to some extent and is a two-step process that must be followed by hydrothermal treatment to obtain HA coatings. Electrophoresis deposition advantageously is not a line-of-sight process, is low cost and simple, provides high deposition rate and produces a wide range of coating thicknesses (from <1 um to >500 um), but disadvantageously is a two-step process requiring densification by sintering which may reduce the purity of the HA coating. Sol-gel deposition advantageously permits coating of complex shapes with coatings having increased homogeneity and fine-grained structures, but disadvantageously requires firing leading to reduced purity of the HA coating. Bio-mimetic deposition advantageously is a low temperature process applicable to any heat sensitive surface including polymers, permits formation of bone-like apatite crystals with high bioactivity and permits incorporation of bone growth stimulating factors and antibiotics, but disadvantageously is a very slow process requiring precise control of process parameters in which obtaining uniform coating is a practical challenge.

Finally, chemical deposition is a process mainly used to prepare HA powders but not to coat HA on a substrate. Few studies of chemical deposition of bioceramic materials are available and process kinetics are poorly understood. In theory, chemical deposition may be able to provide uniform coatings of unlimited thickness on complex shapes, be used to deposit HA on polymer surfaces, and produce a porous top layer to encourage bone ingrowth. No suitable chemical processes are commercially available for coating.

Of the processes described above, most are line-of-sight dependent and/or involve high temperature (over 15,000° C. for plasma spray). It is a challenge for any process that is line-of-sight in nature to produce uniform coating, particularly on sloped and curved surfaces. As for processes that rely on high temperature, they cause decomposition of HA which leads to the formation of impurities such as tetracalcium phosphate ($Ca_4P_2O_9$), amorphous calcium phosphate, α-tricalcium phosphate ($Ca_3(PO_4)_2$), and β-tricalcium phosphate ($Ca_3(PO_4)_2$). These impurities are unstable in the body fluids and cause serious concerns for localized corrosion. The selective dissolution of these impurities may result in an accelerated wear caused by the roughening/scoring of the articulating surface, and this debris will, in turn, make the wear a more severe issue.

It is apparent from the processes described above that biomimetic and chemical processes are neither line-of-sight dependant nor involve high temperature operation. Biomimetic coating is an approach that consists of immersion of metal implants in simulated body fluids (SBF) at a physiologic temperature and pH. HA coating, the major component of bone, grows in a way similar to the natural bone growth in our body. This process produces HA coating with desirable properties such as high purity and bioactivity. Another uniqueness of this process is its capability to incorporate antibiotics (e.g. tobramycin), proteins and bone growth stimulators (e.g. osteogenics). However, although SBF mimics the inorganic composition, pH, and temperature of human blood plasma, achieving a reasonable coating thickness for practical applications takes a long time. Long immersion time (7-14 days) with daily refreshment of SBF's is required. The difficulty results from the metastability of SBF and the process requires replenishment and a constant pH to maintain supersaturation for apatite crystal growth. As a result of the low solubility product of HA and the limited concentration range for the metastable phase, this operation is extremely difficult and might lead to local precipitation or uneven coatings. Such an intricate and long process can hardly be tolerated in the prostheses coating industry.

Chemical coating processes produce HA coatings at low temperature and are line-of-sight independent. Theoretically, chemical processes can produce uniform coatings of unlimited thickness on complex shapes. The deposition rate of chemical HA coating is significantly higher than the biomimetic process due to significantly higher and controllable process parameters. Unfortunately, little is known about its chemical reaction kinetics and the process is used mainly for producing HA powder.

There remains a need in the art for a chemical process for coating a bioceramic material, e.g. hydroxyapatite (HA), on a surface of a substrate.

SUMMARY OF THE INVENTION

There is provided a process for coating a surface of a metal-containing substrate with a bioceramic material, comprising: activating the surface of the metal-containing substrate by applying a voltage to the substrate in a liquid containing an electrolyte; and, immersing the substrate in a deposition solution containing the bioceramic material or precursors for the bioceramic material to form a coated substrate.

There is further provided a process for coating a surface of a metal-containing substrate with a bioceramic material, comprising: activating the surface of the metal-containing substrate by applying a voltage to the substrate in a liquid containing an electrolyte; immersing the substrate in a deposition solution containing the bioceramic material or precursors for the bioceramic material to form a coated substrate; and heat treating the coated substrate.

There is yet further provided a metal-containing substrate coated with a bioceramic material.

There is still yet further provided a prosthesis comprising a metal-containing substrate coated with a bioceramic material.

In comparison to prior art processes, e.g. plasma spray processes, processes of the present invention advantageously permit the formation of purer bioceramic coatings which contain fewer impurities leading to fewer imperfections or holes in the coating leading to more durable coatings. Further, uniform coatings on complex geometries may be achieved with relative ease. Also, smaller particle sizes in the coating may be obtained. Furthermore, the present processes are simpler and less expensive than prior art processes. The present processes may be conducted at lower temperatures; they are not line-of-sight dependent; they have excellent scalability; and they incur low capital investment and lower maintenance and operation cost.

Activation of the Substrate:

The present processes involve activating the surface of a metal-containing substrate by applying a voltage to the substrate in a liquid containing an electrolyte. Electrochemical activation of the surface sensitizes the surface to deposition of the bioceramic material during the coating process.

Voltage may be applied to the substrate by DC current. Applied voltage may result in polarization of the surface of the substrate. Preferably the substrate is used as an anode and the voltage is applied anodically. If desired, an AC perturbation may be superimposed over the applied voltage. The applied voltage (or applied average voltage in the case of an applied voltage with an AC perturbation) is preferably in a range of from about 1 V to about 25 V, preferably from about 1 V to about 20 V, more preferably from about 2 V to about 20 V, even more preferably from about 7.5 V to about 12.5 V. Application of too high a voltage during activation may ultimately result in poor coating performance.

Voltage may be applied for any time duration that suitably activates the surface, preferably not less than about 1 minute. More preferably, the duration over which voltage is applied is about 30 minutes or more. Current density is preferably in a range of from about 0.05 A/cm$^2$ to about 0.2 A/cm$^2$, more preferably from about 0.08 A/cm$^2$ to about 0.18 A/cm$^2$, even more preferably from about 0.1 A/cm$^2$ to about 0.15 A/cm$^2$.

Magnitude of applied voltage, time duration and current density during activation of the substrate surface may ultimately affect coating thickness. Activation may be conducted at any convenient temperature provided the liquid containing the electrolyte remains in a substantially liquid state.

Activation of the surface of the substrate is performed in a liquid-based system, for example a solution of an electrolyte or a molten electrolyte. Solution-based systems are preferred. Solution-based systems have a solvent, for example water, ammonia, etc., and an electrolyte The electrolyte is chosen to provide a negative charge to the surface of the substrate. For example, the electrolyte may be a basic electrolyte that generates anions in the solvent, the anions providing a negative charge on the surface of the substrate. The solvent system is preferably water. The electrolyte is preferable a base or mixture of bases, for example alkali metal hydroxides, alkaline earth metal hydroxides or mixtures thereof. Some suitable electrolytes are sodium hydroxide, potassium hydroxide, lithium hydroxide, calcium hydroxide or mixtures thereof. Sodium hydroxide, potassium hydroxide or mixtures thereof are particularly preferred.

In solution-based systems, the electrolyte may be present in any suitable concentration that results in activation of the surface of the substrate. Preferably, the concentration is in a range of from about 0.1 M to about 20 M, more preferably from about 5 M to about 15 M.

In one embodiment of the invention, activation of the substrate surface may be performed with DC current having a current density of about 0.1 A/cm$^2$ at an applied voltage of about 10 V for about 30 minutes in a 10 M aqueous solution of sodium hydroxide.

Activation may also include sonication. Sonication during activation, for example with ultrasound, may enhance the coating process when coating is performed over longer periods of time (e.g. 24 hours or more).

The metal-containing substrate is any material comprising a metal which can be activated as previously described and on to which a bioceramic material can be coated. The metal-containing material may be, for example, a pure metal, an alloy or a metal-containing composite. Metal-containing composites may be, for example, metal-containing ceramics, or composites of one or metals and a polymer.

Examples of some metals that may be present in the metal-containing substrate are Ti, Zr, Cr, Co, Au, Pt, Ag, Ni, Cu, Mg, Ca, and stainless steel. Metal-containing substrates containing a Group 4B metal are of particular note. In one embodiment, the metal-containing substrate contains Ti, Zr or mixtures thereof. Ti-containing materials are preferred, for example Ti alloys or Ti-containing composites (e.g. Ti-HDPE composite). A particularly preferred substrate is Ti6Al4V alloy.

Coating of the Substrate:

In order to coat the substrate to form a coated substrate, the activated substrate is immersed in a deposition solution containing bioceramic material or precursors for the bioceramic material. Precursors are chemical entities which when combined, for example through chemical reaction, form the bioceramic material. The bioceramic material forms on to the surface of the substrate forming a coating.

The bioceramic material deposited on the surface of the substrate is preferably hydroxyapatite (HA). Preferably, the deposition solution contains precursors for HA, for example calcium ions and orthophosphate ions. Calcium ions and orthophosphate ions may be accompanied by counter ions. The deposition solution may contain other components, for example other salts (e.g. sodium, potassium and/or magnesium salts having counter-anions, for example chloride, bicarbonate and/or sulfate).

The deposition solution comprises a solvent and either bioceramic material, precursors for the bioceramic material or a mixture thereof dissolved therein. For HA coating, the solvent is preferably water. HA has a tendency to precipitate from aqueous solution, particularly at high pH. It is desirable to deactivate the deposition solution by reducing the pH of the solution to enhance selective formation of HA coating on the substrate. At the same time, it is preferable to have a saturated solution of HA or HA precursors to increase deposition rate of the HA on to the substrate. Preferably, the pH is less than about 8, more preferably in a range of from about 6 to about 8. If the pH of the deposition solution is too low, the solution may act to deactivate the surface of the substrate leading to poorer coating performance.

The pH of the deposition solution may be lowered with pH adjusting agents, for example acids (e.g. hydrochloric acid, phosphoric acid, etc.) to reduce unwanted precipitation of HA. In one embodiment buffers containing HCl or TRIS (tris-hydroxymethyl aminomethan) are used to adjust the pH.

During deposition it is desirable, although not necessary, to replenish the deposition solution with more HA or HA precursors in order to maintain a saturated solution of HA or HA precursors to keep the HA deposition rate substantially constant. Replenishment of the deposition solution may be conducted at any suitable time. Preferably, replenishment occurs at regular intervals, for example every 5 to 60 minutes. Replenishment increases coating growth on the substrate, and more frequent replenishments lead to more coating.

Activation of the substrate surface together with deactivation of the deposition solution leads to coating of the substrate surface rather than precipitation of HA in the solution. Further, by selectively activating a part of the substrate, it is possible to selectively coat that part. Surprisingly, the coating process appears to be "autocatalytic" in that the initial covering of the surface of the substrate does not inhibit further coating.

Additional materials may be incorporated into the coating. Such incorporation may be achieved by including one or more of the additional materials in the deposition solution. Inclusion of the one or more additional materials may be effected at any time during the coating process. For example, additional material may be included in the solution throughout the coating process, only at the beginning of the coating process, only at the end of the coating process, in the middle of the coating process, or at staggered intervals during the coating process For medical applications, additional materials may be, for example, bone growth stimulating factors, antibiotics, proteins, hormones, etc.

The substrate may be immersed in the deposition solution for any suitable length of time to form a coating on the substrate surface. Longer immersion times lead to thicker coatings. The substrate may be immersed in the deposition solution for a duration of 0.5 hours or more. Durations of 10 hours or more, preferably 15 hours or more lead to coating thicknesses acceptable for medical applications. Coating thicknesses of up to 50 μm or more can be achieved.

Coatings produced by the present process have excellent morphological characteristics. For example, average grain size is smaller than in coatings produced by prior art processes. By the process of the present invention it is possible for the coating to have an average grain size in the nano-scale, for example less than 20 nm in size, particularly in a range of about 10-20 nm in size. Further, nanoporous structures can be formed having pore diameters less than 800 nm, for example 200-500 nm. Such pore sizes are favourable for encouraging bone growth into the surface of a coated implant.

One of the problems with prior art processes is that HA decomposes, particularly at high temperatures, to form other calcium phosphate compounds which contaminate the coating. Such contaminants lead to imperfections or holes in the coating leading to a decrease in durability. The present process permits deposition of very pure HA coatings with significantly reduced levels of contaminants since HA is selectively deposited on the substrate under gentle conditions, leading to more durable coatings.

Heat Treatment of the Coated Substrate:

After coating the substrate with the bioceramic material, it may be desirable to heat treat the coated substrate to increase bond strength of the coating on the substrate. Heat treatment is preferably performed at a temperature below the temperature at which HA begins to decompose, which is about 800°

C. More preferably, the heat treatment temperature is in a range of from about 350° C. to about 800° C., for example from about 350° C. to about 650° C., or from about 350° C. to about 600° C., or from about 350° C. to about 550° C., or from about 500° C. to about 650° C., or from about 500° C. to about 600° C., or from about 550° C. to about 650° C. In one embodiment, a temperature of about 550° C. may be used. Heat treatment is preferably conducted in a gaseous medium, for example air, argon, neon, helium, nitrogen or mixtures thereof. In situations where only part of a substrate is to be coated, it is sometimes desirable to conduct heat treatment in a gas that is inert to the substrate to reduce the possibility of damaging the substrate, for example through oxidation. Heat treatment may be conducted for any suitable length of time, for example for 0.5 hours or more, particularly for about 1-2 hours. Heat treatment can lead to an increase in coating bond strength of over four times. Coating bond strengths of 24 MPa or more can be achieved.

Applications:

Processes of the present invention are useful for any application in which the coating of a bioceramic material on a metal-containing substrate is desired. The processes are particularly useful in the fabrication of medical devices, e.g. prostheses, especially prosthesis for replacing bone tissue. Prostheses include, for example, replacements for limbs (e.g. arms and legs), digits (e.g. fingers and toes), facial bones, hip bones, spinal bones, and parts thereof. Prostheses may be fully or partially implanted in a body of an animal, for example a human.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

Figure 1:
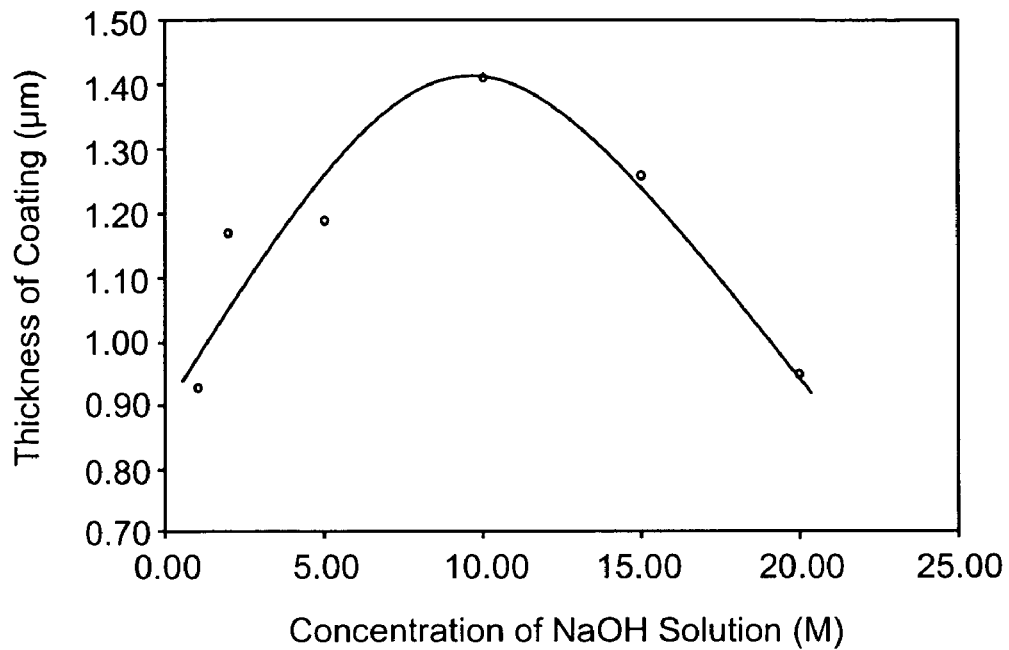
FIG. 1 is a graph of coating thickness (μm) as a function of NaOH concentration (M)

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

Preparation of Substrate:

A 10 mm×10 mm×1.7 mm plate of Ti6Al4V-ELI (extra-low interstitial) alloy formed in accordance with ASTM standard F136-98 having a chemical composition (wt %) of C 0.02, N 0.008, Fe 0.213, Al 6.16, V 3.92, O 0.12 and Ti balance (available from RMI Titanium Company, Mississauga, Canada), was mechanically polished using SiC paper #400 and #600, and 9 μm Al$_2$O$_3$ paper. A titanium wire was spot-welded to the plate for handling. The plate was ultrasonically cleaned for 10 minutes in acetone, then 10 minutes in ethanol and then 10 minutes in deionized water. The cleaned plate was then etched for 10 minutes in a dilute HF acid solution, rinsed in deionized water, ultrasonically cleaned in deionized water for 10 minutes and then dried with cold air.

Activation:

One Ti6Al4V alloy plate prepared as described above was used as the working electrode in an electrochemical cell in the activation of the plate surfaces. Two other Ti6Al4V plates cleaned in ethanol were used as counter electrodes, but the plates of the counter electrode had surface areas that were at least twice as large as the surface areas of the plates of the working electrode. Activation of plate surfaces of the working electrode for each example was accomplished electrochemically by application of a DC voltage to the plates immersed in an aqueous solution of NaOH according to parameters listed in Table 1. In experiments where the effect of ultrasound was investigated, ultrasound at a frequency of 40±2 KHz was applied during activation. In experiments where the effect of ultrasound was not under investigation, ultrasound was not used.

TABLE 1

| Ex. | NaOH conc. (M) | Voltage (V) | Current density (A/cm$^2$) | Time (min) | Temp (° C.) |
|---|---|---|---|---|---|
| A1  | 1   | 5    |  | 30 | Ambient |
| A2  | 2   | 5    |  | 30 | Ambient |
| A3  | 5   | 5    |  | 30 | Ambient |
| A4  | 10  | 5    |  | 30 | Ambient |
| A5  | 15  | 5    |  | 30 | Ambient |
| A6  | 20  | 5    |  | 30 | Ambient |
| A7  | 10  | 1    |  | 30 | Ambient |
| A8  | 10  | 2    |  | 30 | Ambient |
| A9  | 10  | 5    |  | 30 | Ambient |
| A10 | 10  | 10   |  | 30 | Ambient |
| A11 | 10  | 12.5 |  | 30 | Ambient |
| A12 | 10  | 15   |  | 30 | Ambient |
| A13 | 10  | 17.5 |  | 30 | Ambient |
| A14 | 10  | 20   |  | 30 | Ambient |
| A15 | 5   | 10   |  | 1  | Ambient |
| A16 | 10  | 10   |  | 1  | Ambient |
| A17 | 5   | 10   |  | 10 | Ambient |
| A18 | 10  | 10   |  | 10 | Ambient |
| A19 | 5   | 10   |  | 30 | Ambient |

TABLE 1-continued

| Ex. | NaOH conc. (M) | Voltage (V) | Current density (A/cm$^2$) | Time (min) | Temp (° C.) |
|---|---|---|---|---|---|
| A20 | 10 | 10 | | 30 | Ambient |
| A21 | 5 | 10 | | 60 | Ambient |
| A22 | 10 | 10 | | 60 | Ambient |
| A23 | 5 | 10 | | 120 | Ambient |
| A24 | 10 | 10 | | 120 | Ambient |
| A25 | 10 | 4.5 | 0.01 | 30 | Ambient |
| A26 | 10 | 4.9 | 0.02 | 30 | Ambient |
| A27 | 10 | 4.8 | 0.03 | 30 | Ambient |
| A28 | 10 | 6.7 | 0.04 | 30 | Ambient |
| A29 | 10 | 25 | 0.05 | 30 | Ambient |
| A30 | 10 | 10 | 0.08 | 30 | Ambient |
| A31 | 10 | 10 | 0.10 | 30 | Ambient |
| A32 | 10 | ? | 0.15 | 30 | Ambient |
| A33 | 10 | 25 | 0.2 | 30 | Ambient |
| A34 | 10 | 10 | | 30 | 25 |
| A35 | 10 | 10 | | 30 | 30 |
| A36 | 10 | 10 | | 30 | 40 |
| A37 | 10 | 10 | | 30 | 50 |
| A38 | 10 | 10 | | 30 | 60 |

Procedure for Coating:

Deposition solutions saturated with hydroxyapatite (HA) precursors were prepared by dissolving sodium chloride (Fluka, ≧99.5%), sodium bicarbonate (Sigma-Aldrich, ≧99.7%), potassium chloride (Fisher, ≧99.6%), sodium orthophosphate (Sigma-Aldrich, >99.0%) and magnesium chloride hexahydrate (Sigma-Aldrich, >99.0%) in deionized water, followed by the addition of 1 M hydrochloric acid to reduce the pH to about 6, then the addition of calcium chloride hexahydrate (Fisher, ≧99.5%) and sodium sulfate (Anachemia, >99.0), and then the addition of 1 M TRIS (tris-hydroxymethyl aminomethan) to adjust the pH of the solution to 6.5. Calcium chloride was added after acidification with hydrochloric acid to reduce the possibility of precipitating hydroxyapatite (HA). Alternatively, the calcium chloride could be added before acidification and the sodium orthophosphate added after acidification.

The various reagents and deionized water were used in amounts to provide a deposition solution with the following concentrations of ions:

| | |
|---|---|
| $Na^+$ | 142.0 mM |
| $K^+$ | 5.0 mM |
| $Mg^{2+}$ | 1.5 mM |
| $Ca^{2+}$ | 12.5 mM |
| $Cl^-$ | 159.0 mM |
| $HCO_3^-$ | 4.2 mM |
| $HPO_4^{2-}$ | 5.0 mM |
| $SO_4^{2-}$ | 0.5 mM |

Concentrations of the ions in the deposition solution are generally similar to concentrations found in blood plasma and simulated body fluid (SBF), although the concentration of calcium ions ($Ca^{2+}$) and orthophosphate ions ($HPO_4^{2-}$) in the deposition solution are five times their concentration in blood plasma and SBF.

To coat a substrate, 175 ml of the deposition solution in a 250 ml beaker were placed in a water bath at 37° C. for 3 min to raise the temperature of the deposition solution to 37° C. Activated Ti6Al4V alloy plates were weighed to five decimal places and immersed in the deposition solution by hanging them in the solution for a desired length of time. After the desired length of time elapsed, coated Ti6Al4V alloy plates were air dried and weighed. The difference between the weight of the coated and uncoated plates gave the weight of the coating material.

Effect of NaOH Concentration in the Activating Solution:

Activated Ti6Al4V alloy plates prepared in accordance with Examples A1-A6 were coated with HA over 30 minutes in accordance with the procedure for coating described above. A graph of coating thickness (μm) as a function of NaOH concentration (M) is provided in FIG. 1. Coating thickness is calculated from weight gain based on fully dense HA. Coating thickness is a maximum when the concentration of NaOH during activation is about 10 M. The activating solution was very viscous when the concentration of NaOH was 20 M. Scanning electron micrographs (SEM) of the coating surfaces revealed that they were all similar in morphologies and plate-like.

Figure 2:
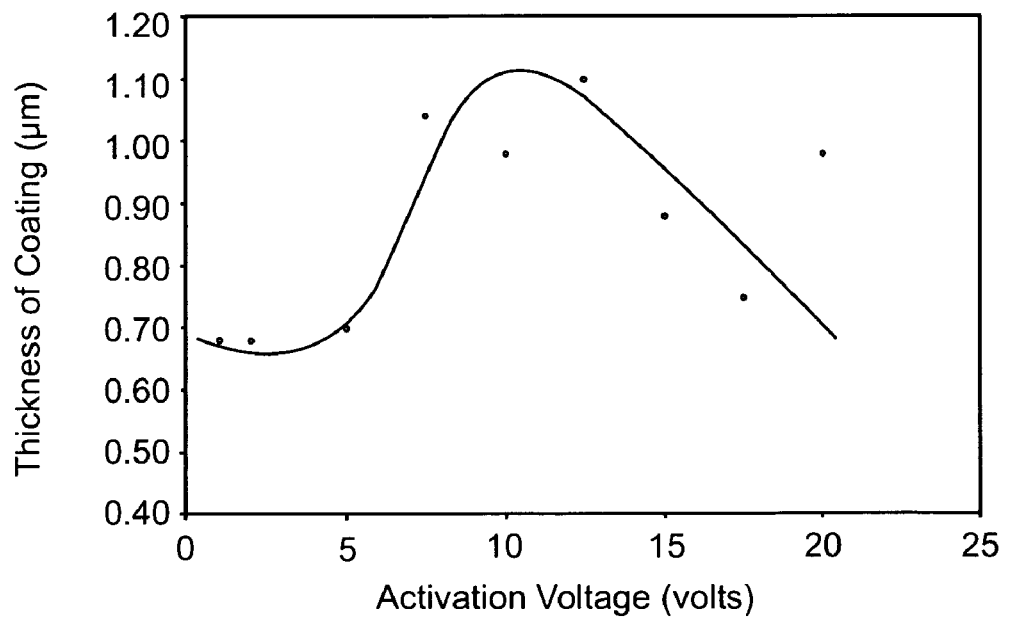
FIG. 2 is a graph of coating thickness (μm) as a function of applied voltage (volts)

Effect of Magnitude of Applied Voltage During Activation:

Activated Ti6Al4V alloy plates prepared in accordance with Examples A7-A14 were coated with HA over 5 hours in accordance with the procedure for coating described above. A graph of coating thickness (μm) as a function of applied voltage (volts) is provided in FIG. 2. Coating thickness is calculated from weight gain based on fully dense HA. Coating thickness is a maximum when the applied voltage during activation is between 7.5 and 12.5 volts, for example around 10 volts. Voltages higher than 20 volts can cause severe reaction, resulting in rounded edges and grooves on the substrate surface, likely due to dissolution of the substrate. SEM results show that coating morphology is affected by the magnitude of the voltage applied during activation. Voltages of 10 volts or less resulted in fine needle-like coatings, while voltages in excess of 20 volts resulted in coarser coatings.

Figure 3:
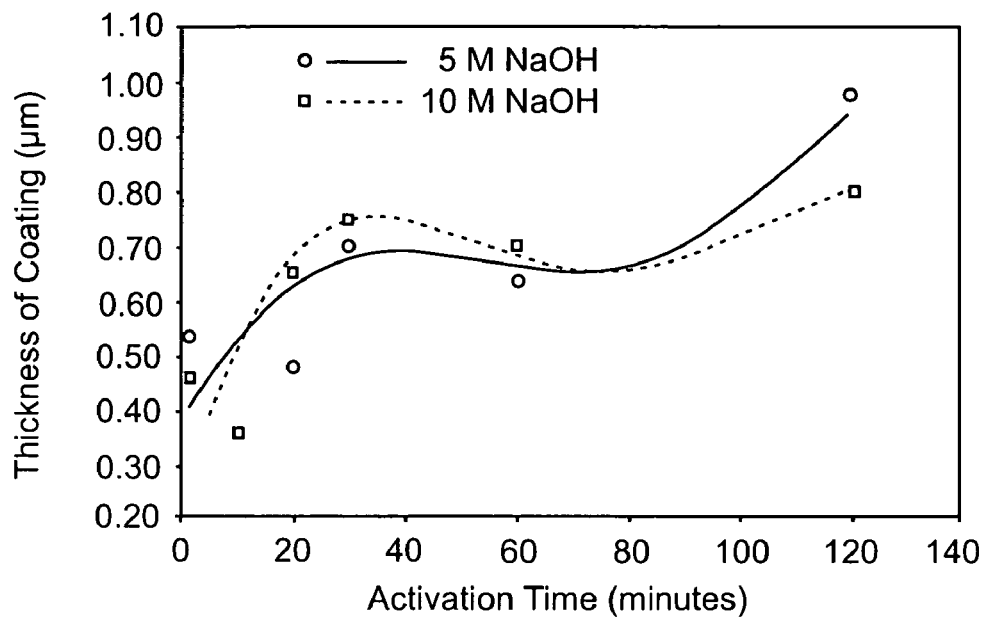
FIG. 3 is a graph of coating thickness (μm) as a function of activation time (minutes)

Effect of Duration of Applied Voltage During Activation:

Activated Ti6Al4V alloy plates prepared in accordance with Examples A15-A24 were coated with HA over 5 hours in accordance with the procedure for coating described above. A graph of coating thickness (μm) as a function of activation time (minutes) is provided in FIG. 3. Coating thickness is calculated from weight gain based on fully dense HA. Coating thickness is a maximum when the activation time is generally 30 minutes or more.

Figure 4:
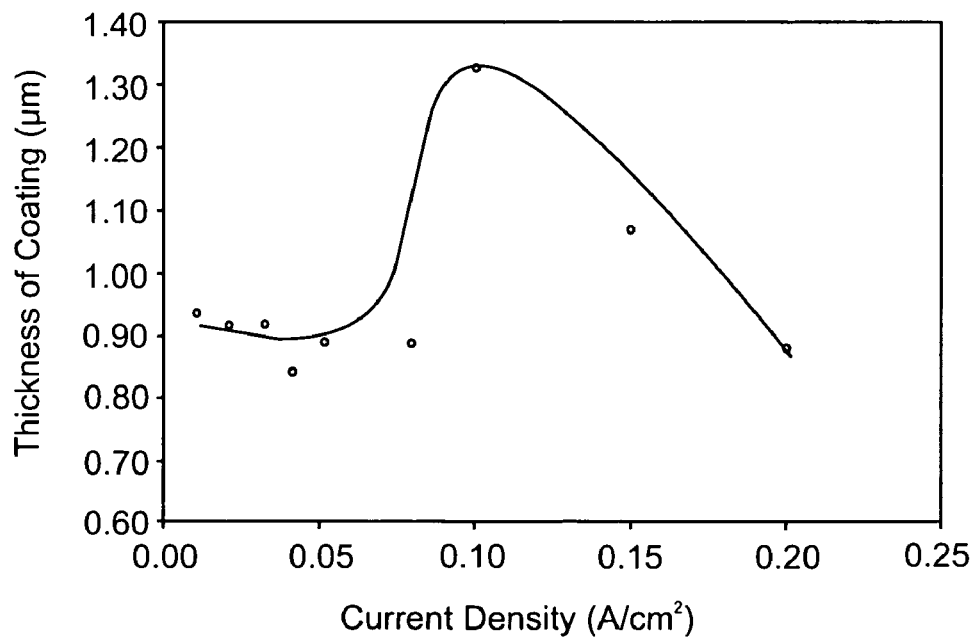
FIG. 4 is a graph of coating thickness (μm) as a function of DC current density (A/cm$^2$)

Effect of Current Density During Activation:

Activated Ti6Al4V alloy plates prepared in accordance with Examples A25-A33 were coated with HA over 5 hours in accordance with the procedure for coating described above. A graph of coating thickness (μm) as a function of DC current density (A/cm$^2$) is provided in FIG. 4. Coating thickness is calculated from weight gain based on fully dense HA. Coating thickness is a maximum when the current density is around 0.1 A/cm$^2$. Currently densities greater than about 0.2 A/cm$^2$ can lead to rounded edges and grooves on the surface. SEM confirms that the coatings have plate-like structures at all current densities.

Figure 5:
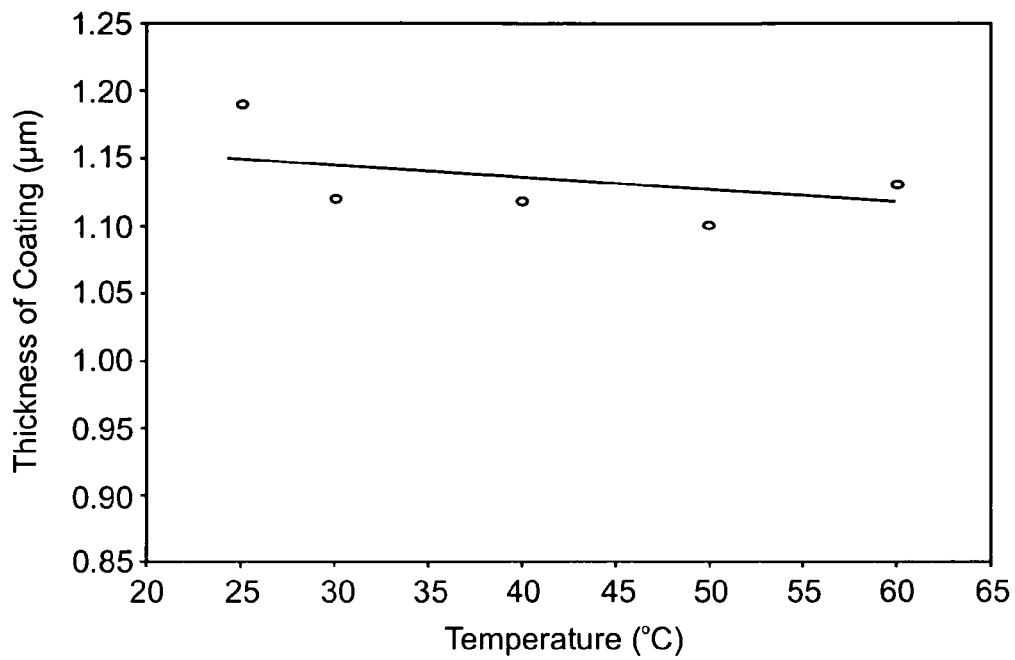
FIG. 5 is a graph of coating thickness (μm) as a function of activation temperature (° C.)

Effect of Temperature During Activation:

Activated Ti6Al4V alloy plates prepared in accordance with Examples A34-A38 were coated with HA over 5 hours in accordance with the procedure for coating described above. A graph of coating thickness (μm) as a function of activation temperature (° C.) is provided in FIG. 5. Coating thickness is calculated from weight gain based on fully dense HA. It is evident that activation temperature has little effect on coating thickness. SEM indicates that coatings all have needle-like structures.

Figure 6:
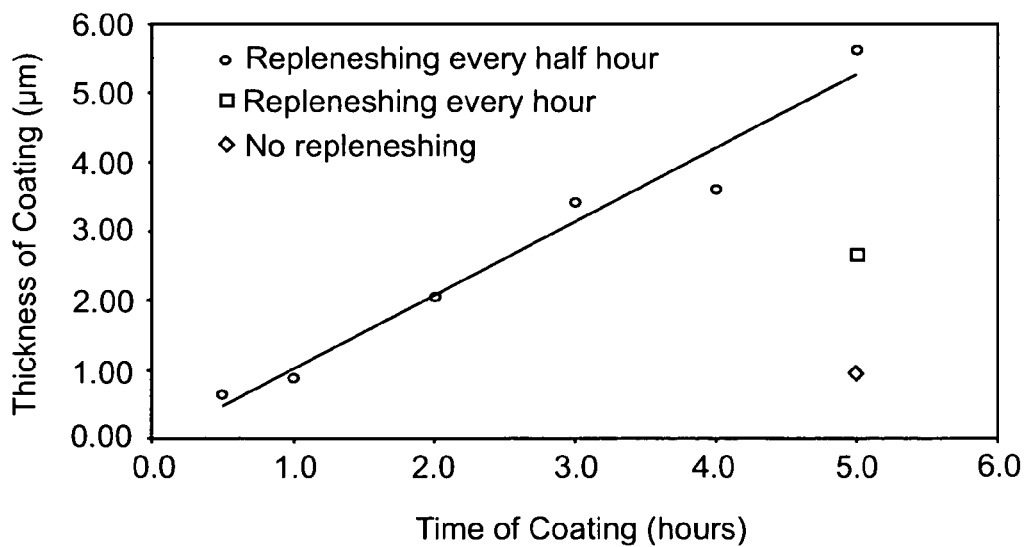
FIG. 6 is a graph of coating thickness (μm) as a function of time (hours) illustrating effect of replenishing deposition solution on growth rate of an HA coating.

Effect of Replenishing HA Solutions During Coating:

The procedure for coating described above was carried out with replenishment of the deposition solution every half hour with freshly made solution. The coated substrates were taken out of solution at time periods of 0.5, 1, 2, 3, 4 and 5 hours. A graph of coating thickness (μm) as a function of time (hours) illustrating effect of replenishing the deposition solution at half hour intervals on the growth rate of the HA coating is provided in FIG. 6. Coating thickness is calculated from weight gain based on fully dense HA. It is evident that replenishing solutions significantly increases coating growth on the substrate.

Two similar experiments, one in which replenishment was not done and one in which replenishment was done at 1 hour intervals confirmed that more frequent replenishing leads to a greater amount of coating on the substrate surface.

In the experiment where replenishment was done at half hour intervals, SEM indicated that morphologies of coated Ti6Al4V substrates at different time periods have a bone-like structure, and to some extent a crystal-like structure, covering the whole surface of the substrate. After 3 hours, the coating grows to such a thickness that the coating starts to crack, likely due to either internal stress or drying. The morphology of the coating at a half hour indicates that HA coating initiates from some active areas and grows in a spherical shape extruding on the surface. Gradually valleys around the spherical extrusions start to be covered by HA coating leading to a more uniform coating surface with time.

HA coating after 5 hours of coating with replenishing solution every one hour leads to more crystal-like coating morphologies, compared to the bone-like or less crystal-like morphologies indicated above. There are more cracks in the coating with less frequent replenishing.

Growth of HA Coatings:

A longer term coating process was performed in which HA was coated on a Ti6Al4V substrate for 15 hours with replenishment of the deposition solution every half hour. A linear relationship between coating duration and coating thickness was observed. Within 15 hours the coating thickness reached about 50 µm, which is an acceptable thickness for hydroxyapatite coating in medical applications. Observed coating thickness was measured from an SEM of a cross-section of the coated substrate. Coating thickness was not a calculated value in this case. The coating looks dense and tightly attached to the substrate, and only a small amount of coating close to the substrate was broken off during grinding and polishing processes. Coating thickness at 10 hours of coating was determined to be about 33 µm as indicated by energy dispersive X-ray spectroscopy (EDX) based on analysis of Ca content.

Figure 7:
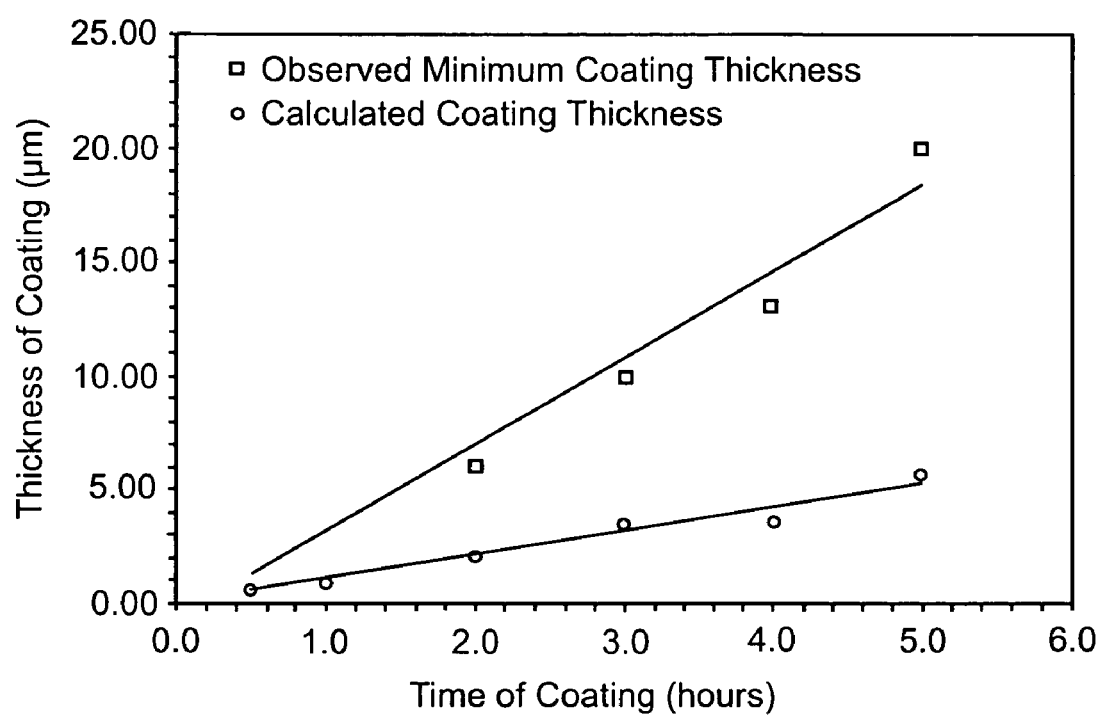
FIG. 7 is a graph of coating thickness (μm) as a function of time (hours) comparing calculated and minimum observed coating thicknesses.

Relationship Between Calculated and Observed Coating Thickness:

A comparison between calculated and observed coating thicknesses was undertaken. Coating experiments were conducted in which activation was done at room temperature in a 10 M NaOH solution at a constant DC voltage of 10 V for 30 minutes. Coating was performed at pH 6.50 at a temperature of 37° C. in a deposition solution as described in the procedure for coating above. The deposition solution was replenished every half hour. Results are provided in FIG. 7 and Table 2. Minimum observed coating thickness is much greater than calculated thickness and appears to be linearly related to duration of coating.

TABLE 2

| Time of Coating (hours) | Calculated Coating Thickness (µm) | Observed Coating Thickness (µm) |
|---|---|---|
| 0.5 | 0.04 | — |
| 1.0 | 0.90 | 4.5 |
| 2.0 | 2.05 | 6 |
| 3.0 | 3.44 | 10 |
| 4.0 | 3.60 | 13 |
| 5.0 | 5.63 | 20 |

Characterization of HA Coatings:

HA coatings on Ti6Al4V substrates produced in accordance with the present invention are of very high purity and are strongly bonded to the substrate.

Strong bonding between the coating and the substrate results from formation of a strong initial layer with inter-diffusion of elements from both the substrate and the coating. EDX line analysis conducted as a line scan perpendicular to the boundary line from the coating to the substrate confirms the existence of a 2-3 µm thick initial diffusion layer close to the substrate. EDX analysis conducted as a line scan parallel to the boundary line between the coating and the substrate further confirms that the initial diffusion layer is an inter-diffusion layer of Ti, Ca and P.

Figure 8:
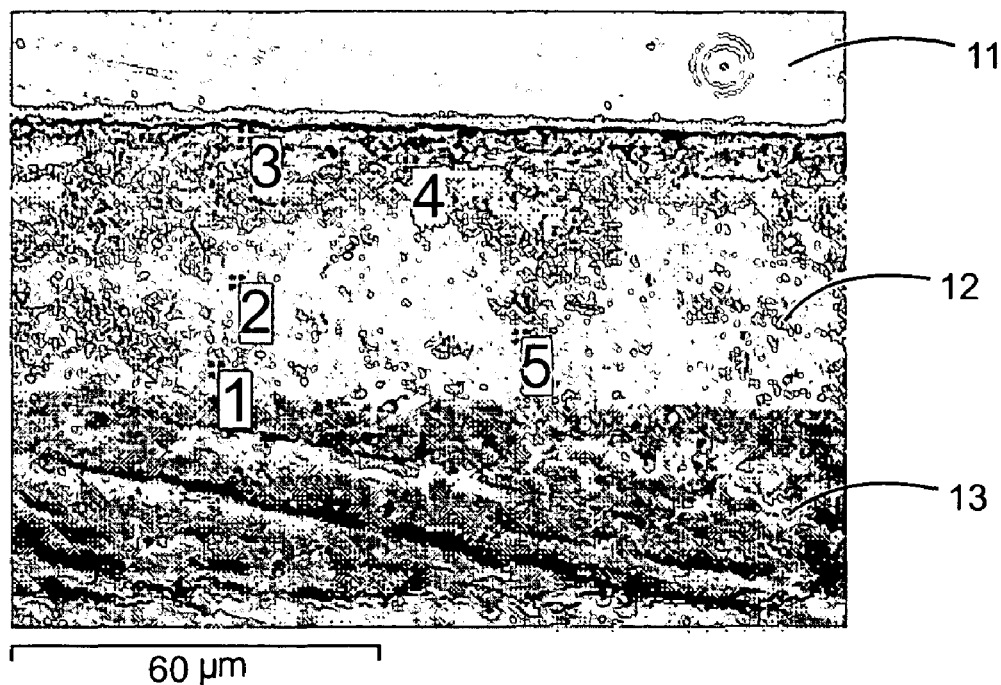
FIG. 8 is a scanning electron micrograph showing a cross-section of a coated substrate with locations of EDX point analysis measurements thereon.

EDX point analysis also confirms that the inter-diffusion layer exists. Referring to FIG. 8, a scanning electron micrograph shows a cross-section of a coated substrate with locations of EDX point analysis measurements 1-5 indicated thereon. Substrate 11 is coated with hydroxyapatite 12 which is covered with a layer of expoxy resin 13. The results of EDX point analysis on the hydroxyapatite (HA) coating and corresponding ratios of Ca/P are listed in Table 3.

TABLE 3

| | EDX analysis (atomic percentage) of coating | | | | | | | |
|---|---|---|---|---|---|---|---|---|
| Measurements | C | O | P | Cl | Ca | Ti | V | Ca/P |
| 1 | 67.77 | 16.43 | 5.81 | 0.52 | 9.47 | | | 1.63 |
| 2 | 58.04 | 18.72 | 8.33 | 0.56 | 14.35 | | | 1.72 |
| 3 | 21.80 | | | | 21.47 | 51.55 | 5.19 | N/A |
| 4 | 32.71 | 25.72 | 5.25 | | 21.47 | 13.68 | 1.23 | 4.08 |
| 5 | 64.56 | 18.11 | 6.36 | 0.36 | 10.59 | | | 1.67 |

Measurement 4 shows that Ca, Ti and V co-exist at the initial coating layer. Since Measurements 1, 2 and 5 are away from the inter-diffusion layer, EDX analysis of these points is not influenced by the substrate and the ratio of Ca/P should be the actual ratio of Ca and P existing in the coating. The average of Measurements 1, 2 and 5 is 1.67, which is exactly the atomic ratio of Ca/P in stoichometric hydroxyapatite $(Ca_{10}(PO_4)_6(OH)_2)$. This confirms that the formed coating is pure HA.

Measurements 3 and 4 are influenced by the inter-diffusion layer and the Ca/P ratio is far away from hydroxyapatite. There is no P detected at Measurement 3 and much more Ca than P is detected at Measurement 4, possibly indicating that Ca first reacts with titanium oxide and favorably deposits on the substrate at the activated substrate surface as amorphous $CaTiO_3$, while the P participates at a later stage as the $CaTiO_3$ incorporates phosphate ion to form hydroxyapatite on the surface. Measurement 3 is closer than Measurement 4 to the substrate, thus there is no P detected at Measurement 3. P gradually deposits and is detected at Measurement 4.

X-ray diffraction (XRD) analyses of commercial crystallized hydroxyapatite powder (PENTAX Corporation, Tokyo, Japan) and of powders obtained from coatings of the present invention confirm that the coatings of the present invention are substantially pure hydroxyapatite (HA). The commercial HA XRD pattern matches very well with the standard XRD pattern of HA in the JCPDF card (Joint Committee on Powder Diffraction Standards—Powder Diffraction Files). Major patterns of the powders from coatings of the present invention match very well with the commercial HA powders.

Coatings formed on substrate surfaces were analyzed with a Perkin Elmer FTIR (Fourier Transform Infrared Spectroscopy) Instrument (Spectrum BX), in a scanning range between 4000 $cm^{-1}$ and 400 $cm^{-1}$ with 216 scans per sample. Spectra obtained show characteristic bands of HA along with additional bands ascribed to associated $H_2O$.

Characteristic FTIR bands of hydroxyapatite corresponding to the stretching vibration of $PO_4^{3-}$ can be observed in the range of 1200-900 $cm^{-1}$, which in this investigation are at 1119 $cm^{-1}$, 1048 $cm^{-1}$, 1036 $cm^{-1}$ and 979 $cm^{-1}$. Deformation vibrations of $PO_4^{3-}$ are at 603 cm$^{-1}$, 572 cm$^{-1}$, 471 cm$^{-1}$ and 422 cm$^{-1}$. Hydroxyl (OH$^-$) bands are at 3458 cm$^{-1}$ and 617 cm$^{-1}$. Bands located in the range of 3900 cm$^{-1}$ to 3500 cm$^{-1}$ and 1900 cm$^{-1}$ to 1400 cm$^{-1}$ can be assigned to associated $H_2O$ in the coating, the result of a long period of exposure in the atmosphere.

With increasing duration of coating, intensities of the hydroxyapatite FTIR bands significantly increase, indicating a significant increase in coating thickness starting from a time of about 180 minutes. The characteristic bands of HA split after about 180 minutes, indicating that the formed HA may be starting to crystallize. Broad and not-split bands of HA at 120 minutes illustrate that the initially deposited HA is in an amorphous or poorly crystallized phase. The characteristic FTIR band of $CO_3^{2-}$ is not very intense up to about 120 minutes of coating, and is significantly more intense after 180 minutes of coating, indicating an increase in carbonate content as coating proceeds.

Figure 9:
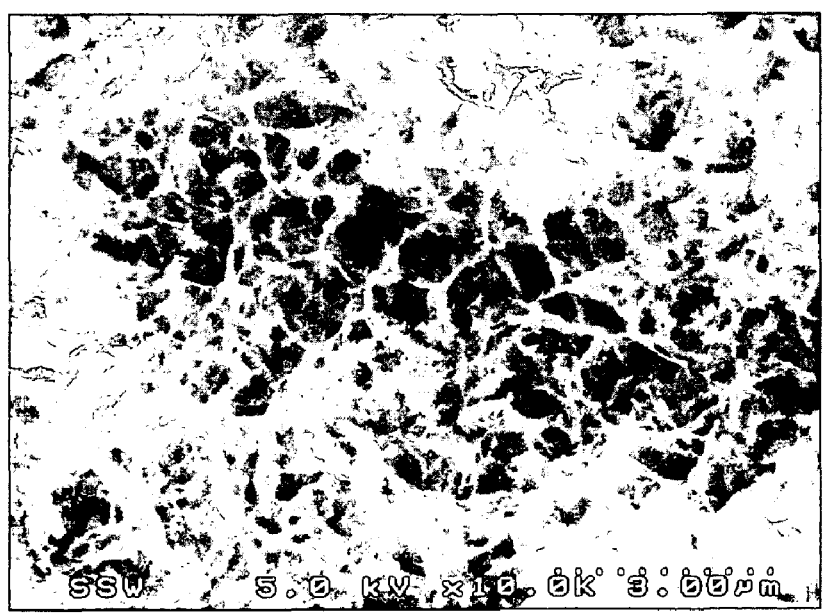
FIG. 9 is a scanning electron micrograph of an HA coating showing pore size.

Scanning electron microscopy (SEM) of the formed HA coating (FIG. 9) shows that pore sizes of the coating are on the nano-scale. Pore diameters are on the order of 200-500 nm.

Figure 10:
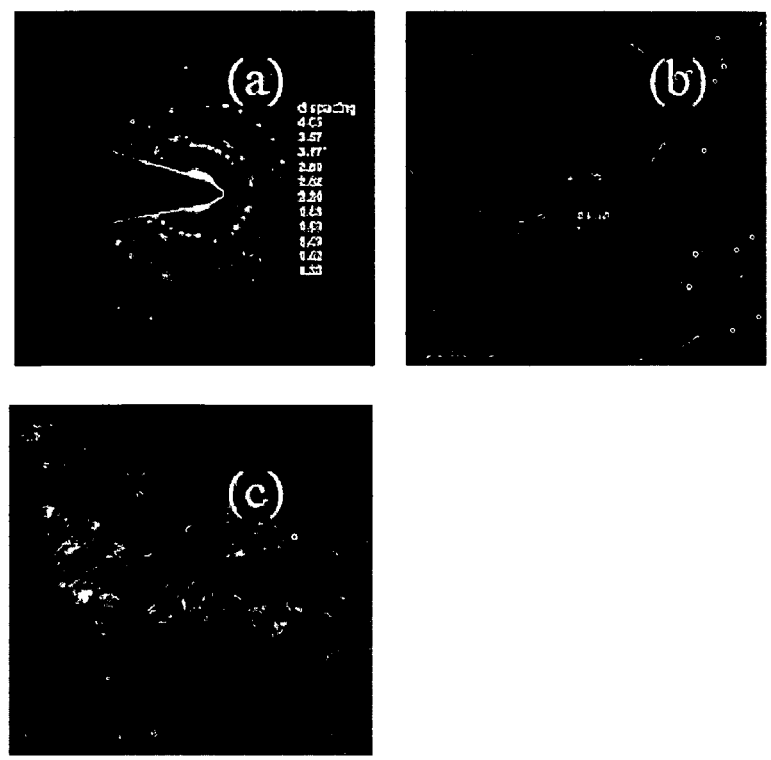
FIG. 10a is a diffraction pattern from transmission electron microscopy (TEM) analysis of an HA coating.
FIG. 10b is a transmission electron micrograph showing crystal planes inside a grain of an HA coating.
FIG. 10c is a transmission electron micrograph showing grains of a single plate of an HA coating; and, FIG. 11 is a graph of coating adhesion strength (MPa) as a function of heat treatment temperature (° C.) for heat-treated HA-coated substrates.

Diffraction pattern from transmission electron microscopy (TEM) analysis (FIG. 10a) shows that the formed HA coating is crystalline with a measured d-spacing that matches pure HA. The formed HA coating has nano-scale grain size of less than 20 nm (FIG. 10b). Morphologies of a single HA plate also show that the grain is less than 20 nm in size (FIG. 10c).

Heat Treatment:

HA-coated Ti6Al4V substrates were prepared by coating an activated substrate of Example A31 using the Procedure for Coating described above. Coated substrates were heat treated in a furnace (Pyradia, Quebec, Canada) in air for 1 hour. Heat treatment experiments were performed at temperatures of 350° C., 450° C., 550° C., 650° C., 750° C. and 850° C.

Figure 11:
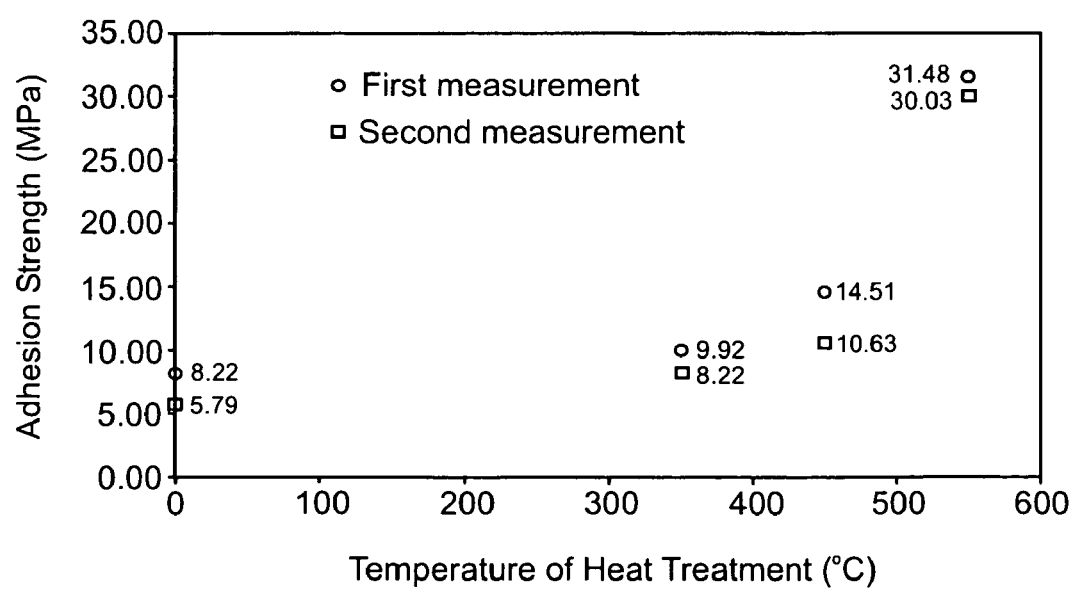

FIG. 11 is a graph of coating adhesion strength (MPa) as a function of heat treatment temperature (° C.) for heat-treated HA-coated substrates. A repeated testing confirmed the trend and the values of adhesion strength. Adhesion strength increased dramatically between temperatures of about 350° C. and about 550° C. from about 9 MPa to about 31 MPa, an increase of about 3 to 4 times. Heat-treatment at 650° C. and above can lead to powdering of the coating, rendering the coating more brittle and more easily broken off.

Scanning electron microscopy (SEM) analysis before and after heat-treatment indicate that surface morphologies are similar before and after heat-treatment at temperatures in a range of from about 350° C. to 550° C. After a temperature of 650° C., heat-treatment widens cracks on the surface of the coating and the coating becomes porous. Widening of cracks may be a result of a mismatch between the coefficients of thermal expansion (CTE) of the Ti6Al4V substrate, $TiO_2$ and HA layers. Heat-treatment may cause a small amount of contraction between the substrate and the $TiO_2$ layer, while large expansion between the $TiO_2$ layer and the HA layer may result in severe stresses, which may be released by cracking.

X-ray diffraction (XRD) patterns of heat-treated and untreated samples indicate that crystallinity of the HA coating increases at temperatures of 450° C. and 550° C. with the appearance of new peaks. At 650° C. one new phase appears, which was found to be tricalcium phosphate (TCP), and the coating is mixture of HA and TCP. With increasing temperature beyond 650° C., the concentration of TCP increases. TCP is more readily dissolvable than HA in human body fluids, thus the formation of the TCP is not favorable for medical applications. SEM observations also show that heat treatment at and above 650° C. can cause some morphology changes.

Fracture surface analysis of hydroxyapatite (HA) coatings with and without heat-treatment after adhesion testing indicates that some of the coating still adheres to the substrate, i.e. fractures happen inside the coating instead of between the coating and the substrate, indicating that bonding is strong between the coating and the substrate. More of the coating adheres to the substrate with an increase in heat-treatment temperature, indicating that bonding becomes stronger with an increase on heat-treatment temperature, i.e. heat-treatment strengthens the bonding between the coating and the substrate.

Incorporation of Protein Into HA Coatings:

Attempts were made to incorporate Bone Morphogenic Protein (BMP2) into HA coatings on Ti6Al4V substrates at concentrations of BMP2 of 1 µg/L, 10 µg/L and 50 µg/L by the following general procedure. Step 1: Coating of activated Ti6Al4V substrates was performed in 175 ml beakers for 2 hours with a regular deposition solution without addition of protein. The deposition solution was replenished at half hour intervals. Step 2: Further coating of coated substrates from Step 1 was performed in 50 ml beakers for 3 hours with addition of protein at different concentration. The deposition solution was replenished at one hour intervals. For comparison, other coated substrates from Step 1 were further coated with HA under various conditions without addition of protein. Coating conditions are listed in Table 4 and the coating weight gain is listed in Table 5.

TABLE 4

| | Step 1 | | | Step 2 | | | |
| --- | --- | --- | --- | --- | --- | --- | --- |
| Sample | coating time (h) | interval (h) | solution volume (ml) | coating time (h) | interval (h) | solution vol. (ml) | protein (µg/L) |
| P1 | 2.0 | 0.5 | 75 | | | | |
| P2 | 2.0 | 0.5 | 175 | 3.0 | 1.0 | 175 | 0 |
| P3 | 2.0 | 0.5 | 175 | 3.0 | 0.5 | 50 | 0 |
| P4 | 2.0 | 0.5 | 175 | 3.0 | 1.0 | 50 | 0 |
| P5, P6 | 2.0 | 0.5 | 175 | 3.0 | 1.0 | 50 | 1 |
| P7, P8 | 2.0 | 0.5 | 175 | 3.0 | 1.0 | 50 | 10 |
| P9, P10 | 2.0 | 0.5 | 175 | 3.0 | 1.0 | 50 | 50 |

TABLE 5

| | P1 | P2 | P3 | P4 | P5 | P6 | P7 | P8 | P9 | P10 |
| --- | --- | --- | --- | --- | --- | --- | --- | --- | --- | --- |
| Weight gain (mg/cm$^2$) | 0.67 | 1.87 | 1.28 | 1.08 | 1.15 | 1.35 | 1.15 | 1.15 | 1.14 | 1.30 |
| Average | 0.67 | 1.87 | 1.28 | 1.08 | 1.25 | | 1.15 | | 1.22 | |

SEM indicates that all coatings from Step 1 have a bone-like morphology. For Step 2, SEM indicates that the morphology of HA coatings after coating with solutions having protein at concentrations of 1 μg/L and 10 μg/L is fine and hairy, but the protein is not present in the coating. SEM indicated that the addition of 50 μg/L of protein significantly changed the morphology to a very fine bone-like structure with a large presence of protein. It appears that incorporation of protein into the HA coating may be initiated at a certain minimum concentration of protein. High SEM magnification indicates that protein and HA mingle together in the coating, which is good to sustain protein in the coating. Heat treatment of coatings containing protein may result in protein denaturation or pyrolysis.

Coating of Ti-HDPE Composite:

A Ti-composite was fabricated by infiltrating high density polyethylene (HDPE) at elevated temperature into a porous Ti disk, which was sintered from micro-scale Ti powders. The disks were polished using #400 SiC paper to form a flat surface, and then the disks were subjected to sand-blasting on all the surfaces using #10 alumina powders. To make a through activation on the disks due to the porosities, the activation process was performed for 45 minutes. A regular Ti6Al4V alloy was subjected to the same treatments and coating procedures.

Table 6 shows the weight gain of hydroxyapatite after coating process. More HA coating formed on porous Ti and Ti-HDPE composite disks than on the regular Ti6Al4V alloy. More HA coating formed on the porous Ti than on the Ti-HDPE composite, possibly due to its greater porosity in which some NaOH was trapped, resulting in a more alkaline surface, which is favorable for the formation of HA coating on the surface. Even though more HA coating formed on porous Ti, the surface is not fully covered and the coating is not even. HA coatings on porous Ti have some uncovered areas on the bottoms, and it is difficult to form coatings on the edges and surrounding surfaces. In contrast, HA coating is evenly distributed on the surface of Ti-HDPE composite disks, with the bottoms, edges and surrounding surfaces all fully covered.

TABLE 6

| | Material | | | |
|---|---|---|---|---|
| Ti6Al4V | Ti-HDPE Composite Sample | | Porous Ti | |
| S1 | S2 | S3 | S4 | S5 |
| Weight Gain (mg/cm²) 1.198 | 1.594 | 1.619 | 2.080 | 3.181 |
| Average Weight Gain (mg/cm²) 1.198 | 1.607 | | 2.630 | |

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. Process for coating a surface of a metal-containing substrate with a bioceramic material comprising: activating the surface of the metal-containing substrate by applying a voltage to the substrate in an aqueous solution of an alkali metal hydroxide; and, immersing the substrate in a deposition solution containing the bioceramic material or precursors for the bioceramic material to form a coated substrate.

2. Process of claim 1, wherein the bioceramic material comprises hydroxyapatite.

3. Process of claim 2, wherein the deposition solution contains hydroxyapatite precursors.

4. Process of claim 3, wherein the precursors are $Ca^{2+}$ and $HPO_4^{2-}$.

5. Process of claim 2, wherein the deposition solution is an aqueous solution having a pH of less than 8.

6. Process of claim 5, wherein the pH is in a range of from 6 to 8.

7. Process of claim 2, wherein the metal-containing substrate comprises a Group 4B metal.

8. Process of claim 2, wherein the metal-containing substrate comprises Ti.

9. Process of claim 2, wherein the metal-containing substrate comprises Ti6Al4V alloy.

10. Process of claim 1, wherein the alkali metal hydroxide is present in a concentration of 5-15 M.

11. Process of claim 2, wherein the voltage is in a range of from 2 V to 20 V.

12. Process of claim 2, wherein the voltage is applied as direct current at a current density in a range of from 0.08 A/cm² to 0.18 A/cm².

13. Process of claim 2, wherein the voltage is applied for a period of 30 minutes or more.

14. Process of claim 1, wherein the deposition solution is a saturated solution of hydroxyapatite precursors that is replenished periodically during the coating process.

15. Process of claim 2, further comprising heat treating the coated substrate.

16. Process of claim 15, wherein the heat treating is performed at a temperature in a range of from 350° C. to 650° C.

17. Process of claim 15, wherein the heat treating is performed at a temperature in a range of from 500° C. to 600° C.

18. Process of claim 2, wherein the deposition solution further comprises a protein.

19. Process for coating a surface of a Ti-containing substrate with hydroxyapatite, comprising: activating the surface of the Ti-containing substrate by applying a DC voltage of 7.5-12.5 V at a current density in a range of from 0.08 A/cm² to 0.18 A/cm² to the substrate for 30 minutes or more in an aqueous solution having an alkali metal hydroxide concentration in a range of from 5 M to 15 M; and, immersing the substrate in an aqueous solution of hydroxyapatite precursors at a pH in a range of from 6 to 8 to form a coated substrate.

20. Process of claim 19, wherein the precursors are $Ca^{2+}$ and $HPO_4^{2-}$.

21. Process of claim 20 further comprising heat treating the coated substrate at a temperature in a range of from 350° C. to 650° C.

22. Process of claim 21, wherein the deposition solution is saturated with are $Ca^{2+}$ and $HPO_4^{2-}$ and the deposition solution is replenished periodically with $Ca^{2+}$ and $HPO_4^{2-}$ during the coating process.

* * * * *